United States Patent [19]

Homann et al.

[11] Patent Number: 4,553,553
[45] Date of Patent: Nov. 19, 1985

[54] DEVICE FOR THE DETECTION OF BACTERIA, FUNGI, AND VIRUSES IN BLOOD

[75] Inventors: Ernst Homann, Laudenbach; Michael Nelboeck, Tutzing; Klaus Schlieder, Mannheim; Gernold Bayer, Brühl, all of Fed. Rep. of Germany

[73] Assignee: Boehringer Mannheim GmbH, Mannheim, Fed. Rep. of Germany

[21] Appl. No.: 472,455

[22] Filed: Mar. 7, 1983

[30] Foreign Application Priority Data

Mar. 13, 1982 [DE] Fed. Rep. of Germany ... 8207121[U]

[51] Int. Cl.⁴ .................. B01D 27/00; A61M 5/00
[52] U.S. Cl. ................... 128/749; 604/190; 210/927
[58] Field of Search ............... 128/630, 632, 637, 749, 128/760, 762; 604/190, 110, 406, 111, 184, 222, 4-6; 210/927

[56] References Cited

U.S. PATENT DOCUMENTS

| 3,344,785 | 10/1967 | Hamilton | 604/4 |
|---|---|---|---|
| 3,493,503 | 2/1970 | Mass | 604/190 X |
| 4,008,718 | 2/1977 | Pitesky | 604/190 |
| 4,219,021 | 8/1980 | Fink | 604/248 X |
| 4,261,359 | 4/1981 | Chein | 604/184 |
| 4,261,828 | 4/1981 | Brunner et al. | 210/927 X |
| 4,309,992 | 1/1982 | Dodak et al. | 210/927 X |
| 4,358,376 | 11/1982 | Moriuchi et al. | 210/927 X |
| 4,370,381 | 1/1983 | Horikoshi et al. | 210/927 X |
| 4,384,954 | 5/1983 | Nakashima et al. | 210/927 X |

FOREIGN PATENT DOCUMENTS 2826416 2/1980 Fed. Rep. of Germany ...... 128/749

Primary Examiner—E. Coven
Attorney, Agent, or Firm—Felfe & Lynch

[57] ABSTRACT

A device used in detecting bacteria, fungi, and viruses in blood circulated through a particulate adsorbent material initially in a housing has a piston for pushing the adsorbent material from the housing for the detection. The piston preferably provides one passage for circulating the blood through the adsorbent material in the housing. An O-ring on the piston preferably indicates when the device has been used.

16 Claims, 4 Drawing Figures

DEVICE FOR THE DETECTION OF BACTERIA, FUNGI, AND VIRUSES IN BLOOD

The present invention is concerned with a device for the detection of bacteria, fungi and viruses in blood.

A known device for the detection of bacteria, fungi and viruses in blood has a housing in which is present a particulate adsorbent capable of binding bacteria, fungi and viruses. The adsorbent is suitable for subsequent bacteriological, virological, mycological or electron-microscopic investigation. The housing has two connections for tubes for introducting and removing blood flowing in an extracorporeal circulation, the housing being constructed substantially as a cylinder which is preferably circular in cross-section.

Such a device, which is hereinafter called a diagnostic module, is known from Federal Republic of Germany Patent Specification No. 28 26 416. It is especially useful for the recognitiion of septic complications in patients who, because of some other severe illness, are in intensive care units. As is described in detail in the above-mentioned German Patent Specification, in these cases it is very important that a possible infection by bacteria, viruses or fungi is recognised as quickly as possible and the pathogen is identified in order to combat it as quickly as possible with a specific antibiotic.

Before the invention forming the basis of the above-mentioned German Patent Specification, upon suspicion of a sepsis, a blood culture technique was usually employed. The probability of thereby identifying the pathogen was about 30%, which was much too low. Furthermore, this technique required an immediate bacteriological investigation of the sampled blood. This requirement can only be fulfilled without interruption in hospitals which have a permanent bacteriological service. In other cases, delays are possible, which could be adverse for the chances of recovery of the patients.

The invention described in Federal Republic of Germany Patent Specification No. 28 26 416 provided a decisive advance by providing a device which consists essentially of a housing with two connections through which the blood of the patient flows in an extracorporeal circulation, the housing containing an adsorbent known per se for therapeutic purposes. The inventors of this device recognised that bacteria, fungi and viruses are enriched on the surface of the adsorbent when blood flows therethrough and that this property can be advantageously employed for diagnostic purposes. In order to enrich the pathogens on the adsorbent, the extracorporeal circulation is maintained, for example, for 30 to 60 minutes, whereafter the diagnostic module is removed, then removed, then rinsed through with, for example, physiological saline and subsequently filled with a nutrient medium and preferably incubated at body temperature.

Thereafter, parts of the nutrient solution and of the adsorbent are removed from the housing which, for this purpose, is provided with at least one removal corner. The adsorbent is preferably present in the form of a plurality of small solid bodies as a granulate or the like, a large adsorbing surface area thereby being provided. Since this large surface area can, however, also be achieved by means of a suitable porous structure, the adsorbent can also consist of larger parts, for example it can be in the form of round discs. However, these parts must be such that they are suitable for the subsequent microbiological investigation.

In order to carry this out, appropriate amounts of the nutrient solution and of the adsorbent are, in the case of the known device, removed with, for example, a spatula and applied to an agar nutrient substrate. On this, the micro-organisms present in the blood of the patient and enriched on the surface of the adsorbent or present in the nutrient solution are cultured and subsequently identified by one of the known microbiological processes. Further details are to be found in the above-mentioned Federal Republic of Germany Patent Specification No. 28 26 416, to which reference is here made.

Summarising, the process described in Federal Republic of Germany Patent Specification No. 28 26 416 provides the following advantages in comparison with the previously usual blood culture methods:

(1) Due to the enrichment of the micro-organisms on the adsorbent, the probability of a positive detection of the micro-organisms is increased. This applies especially when, as is frequently the case with patients under intensive care, broad-spectrum antibiotics have already been employed. Given the resulting, initial, especially relatively low concentrations, the chance of a successful culturing of the adsorbent-enriched micro-organisms is increased.

(2) The danger of a falsely positive finding or of the identification of false micro-organisms due to contamination is reduced. The fact that, because of the enrichment of the micro-organisms, extremely sensitive micro-biological detection methods do not have to be used in which the danger of a falsely positive finding originating from a contamination is especially high, thereby plays a considerable part.

(3) In many cases, the speed of detection can be increased because the micro-organism enrichment permits an acceleration of the microbiological detection and especially because obtaining the starting material carrying the micro-organisms, namely the adsorbent, and the subsequent incubation thereof is possible at practically any time so that valuable time is not lost when the extraordinarily demanding blood culture methods and the skilled personnel needed for the evaluation thereof are, for the time being, not available.

In spite of these decisive advantages, the process of Federal Republic of Germany Patent Specification No. 28 26 416 has still not been used to a very great extent because the hitherto known diagnostic modules suffer from considerable disadvantages in practical use. These include, in particular, the removal of the adsorbent material from the housing which previously took place by means of a spatula, made the dosing on to agar plates comparatively difficult and time-consuming, and presented, also, a considerable risk of contamination. Difficulties thereby arose, in particular due to the fact that the particulate adsorbent material frequently stuck together relatively firmly after blood had passed therethrough.

Therefore, it is an object of the present invention so to improve the diagnostic module according to Federal Republic of Germany Patent Specification No. 28 26 416 that a simplified handling is possible, with a reduced danger of contamination. The module is thereby to be constructed in such a manner that it can be manufactured simply and economically, if possible as a disposable part, and is to be available in a sterile manner for the purpose of use.

Thus, according to the present invention, there is provided a device for the detection of bacteria, fungi and viruses in blood comprising a housing in which is present a particulate adsorbent capable of binding bacteria, fungi and viruses. The adsorbent is suitable for subsequent bacteriological, virological, mycological or electron-microscopic investigation. The housing has two connections for tubes for introducing and removing blood flowing in an extracorporeal circulation, the housing being preferably a cylinder, of circular cross-section. A piston operable by means of a piston rod projecting out of the housing is arranged in the housing so as to be slidable between a first position and a second position. In the first position, a hollow space is bounded by the piston, the cylindrical housing wall and a removable cover, in which hollow space there is provided the absorbent when the device is connected to an extracorporeal circulation. In the second position, the hollow space is smaller than in the first position so that, when the piston is moved from the first position to the second position with the cover removed, at least a part of the adsorbent is forced out of the housing.

According to a preferred embodiment of the device according to the present invention, one of the connections for the blood-conducting tubes is a part of the piston rod, the piston rod having a longitudinal bore through which blood can flow. In this case, the device according to the present invention resembles a syringe with a bored-through piston rod, blood thereby being able to flow through this syringe in its totality. Since the piston, however, is to be used for forcing the adsorbent filling out of the syringe, it has a constructional part which can be regarded as being a filter and which acts as a holding element for the adsorbent filling. When absorbent consists of comparatively large particles, the holding element can consist of one or more holes through the piston and smaller than the smallest particles of the adsorbent. When, as is preferred, the adsorbent is in the form of a comparatively fine granulate, the holding element preferably consists of an appropriate sieve or of a holding plate with canals for the blood.

The present invention and the advantages to be achieved therewith are described in the following in more detail, with reference to a preferred embodiment illustrated in the accompanying drawings, in which.

Figure 1:
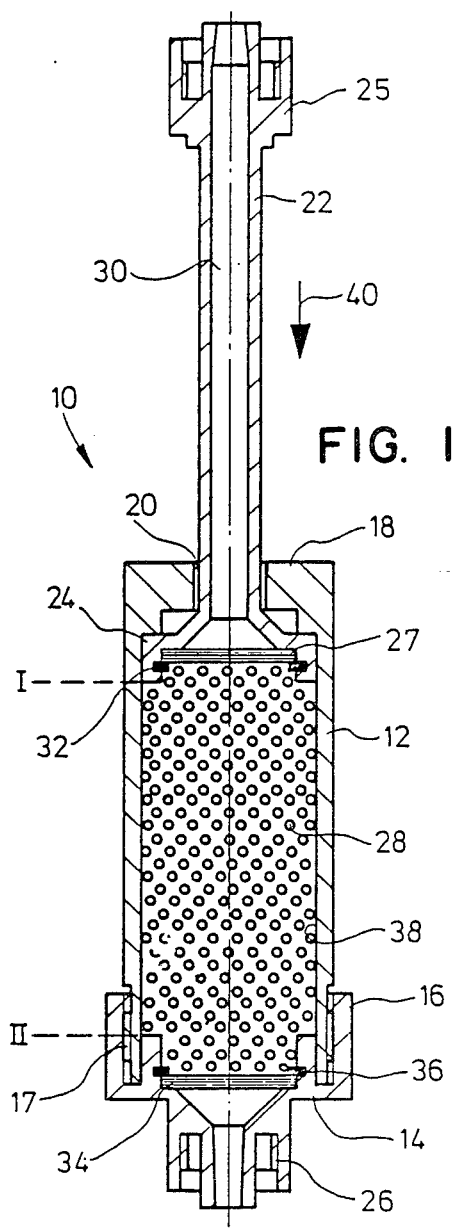
FIG. 1 shows a cross-section through the central unit of the diagnostic module according to the present invention.

In FIG. 1, the diagnostic module is indicated in its totality by 10. It consists essentially of a cylindrically-shaped housing 12, the lower end of which in the drawing is indicated by 14, this end 14 being closed by a cover 16 which is screwed on by means of a thread 17.

The upper end 18 of the housing shown in FIG. 1 is closed except for a bore 20, through which passes a piston rod 22 of a piston 24.

On the end of the piston rod 22 remote from the housing 12, there is provided a first connection 25 for a tube which transports the blood of a patient in an extracorporeal circulation. A second connection 26 of this type is provided in the cover 16. In both cases, these connections are preferably Luer brand connections, such as are conventional in medical technology. In the piston 24, there is provided a sieve 27, which acts as a separating element or filter, i.e. it prevents the adsorbent 28 passing from the hollow space of the cylindrical housing 12 into a bore 30 of the piston rod 22. The separating element is connected with the piston 24 by, for example, a clamping ring 32.

In a corresponding manner, the cover 16 is provided with a separating element 34 and a clamping ring 36.

In FIG. 1, the piston 24 is present in a first position indicated by I. Like the piston in a syringe, it is so constructed that it can slide along the inner wall 38 of the cylindrical housing 12 in the drawing from above downwardly when an appropriate pressure is exerted on the piston rod 22 in the direction of the arrow 40.

Figure 4:
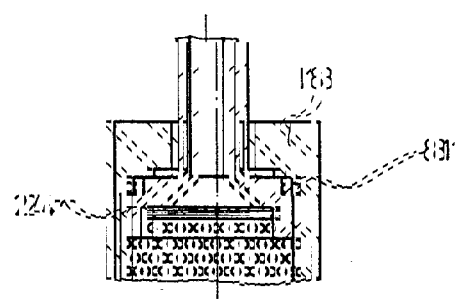
FIG. 4 shows a partial view of a preffered embodiment.

In a further preferred embodiment (FIG. 4), the piston 24 tapers, meaning herein a conical or stepped shape, its diameter in the direction of the piston rod 22 being smaller than in the direction of the cover 16. Drawn over the conical construction or laid into a step of the piston there is provided an O-ring 81 which, in the case of movement of the piston from position I to position II, slips irreversibly from the piston and thus indicates that the piston has been moved. An advantage of this embodiment is that the user can easily ascertain from the position of the O-ring 81 whether the device according to the present invention has been used and thus that parts of the absorbent have already been forced out or whether it is a still sterile and unused device.

For the detection of bacteria, fungi and viruses in the blood of a patient, the device illustrated in FIG. 1 is connected with an extracorporeal circulation so that blood flows from the first connection 25 through the bore 30, the separating element 27, the adsorbent 28, the separating element 34 and the connection 26. This circulation is, as mentioned above, maintained for some time, for example 30 to 60 minutes. Any micro-organisms present in the blood thereby collect on the surface of the particulate adsorbent 28.

Thereafter, the housing must be rinsed through and incubated. For this purpose, it is preferable to use the device illustrated schematically in FIG. 2 in which the diagnostic module 10 is provided with two three-way pieces 50 and 52 which, in the illustrated embodiment, each consists of a three-way stopcock 54 or 56, acting as a closure means, and corresponding tubular connection elements 58.

The three-way stopcocks 54 and 56 connected via tubes 60 and 62 with the connections 25 and 26 of the diagnostic module 10. In principle, they can be formed as one piece with the cover 16 or the piston rod 22 but this can complicate construction.

Figure 2:
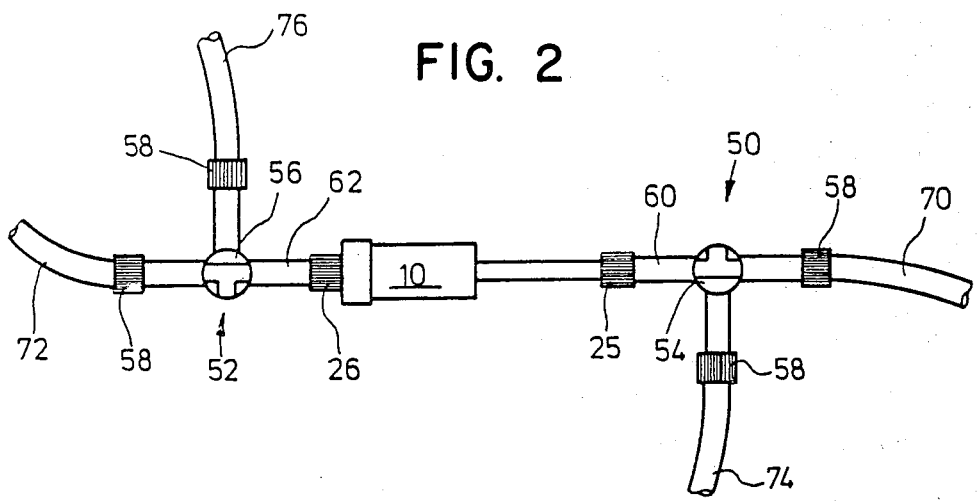
FIG. 2 is a schematic view of a preferred diagnostic module according to the present invention.

In FIG. 2, tubes 70 and 72 serve for the connection of the blood circulation. In the case of the illustrated position of the three-way stopcocks 54 and 56, the blood flows through the device from the tube 70 to the tube 72. An essential advantage of the embodiment illustrated in FIG. 2 is that, in an especially simple manner, after the time necessary for the enrichment of the sought-after bacteria, fungi or viruses on the adsorbent has elapsed, it is merely necessary to bring the three-way stopcocks 54 and 56 into a piston in which the tubes 70 and 72 are closed off from the diagnostic module and, in place thereof, tubes 74 and 76 are connected to the interior of the diagnostic module 10. In the case of this preferred embodiment, this switch over is possible without there being any danger of a contamination.

Through the tube 74, for example, there can now be introduced a rinsing agent current which flows off through tube 76. Thereafter, through the same tubes, the diagnostic module 10 is provided with a nutrient broth.

By appropriate further rotation of the three-way stopcocks 54 and 56, the diagnostic module 10 is finally closed off at both ends. The tubes 70, 74, 72 and 76 can now be removed and the module 10 is placed into an incubation cabinet in order to incubate the micro-organisms in the nutrient solution.

In order to initiate the culturing of a micro-organisms after the incubation step, the diagnostic module is removed from the incubation cabinet and the cover 16 (FIG. 1) is removed. The adsorbent filling 28 can now be forced out of the housing portionwise in a very simple manner and distributed on to appropriate agar plates or other suitable culture media. For this purpose, pressure is exerted (in FIG. 1 from above) on the upper end of the piston rod 22 so that the piston moves from position I illustrated in FIG. 1 downwardly in the direction of the indicated position II. It thereby forces the adsorbent 28 out of the space bounded by the piston 24 and the inner wall 38 of the cylindrical housing 12.

Figure 3:
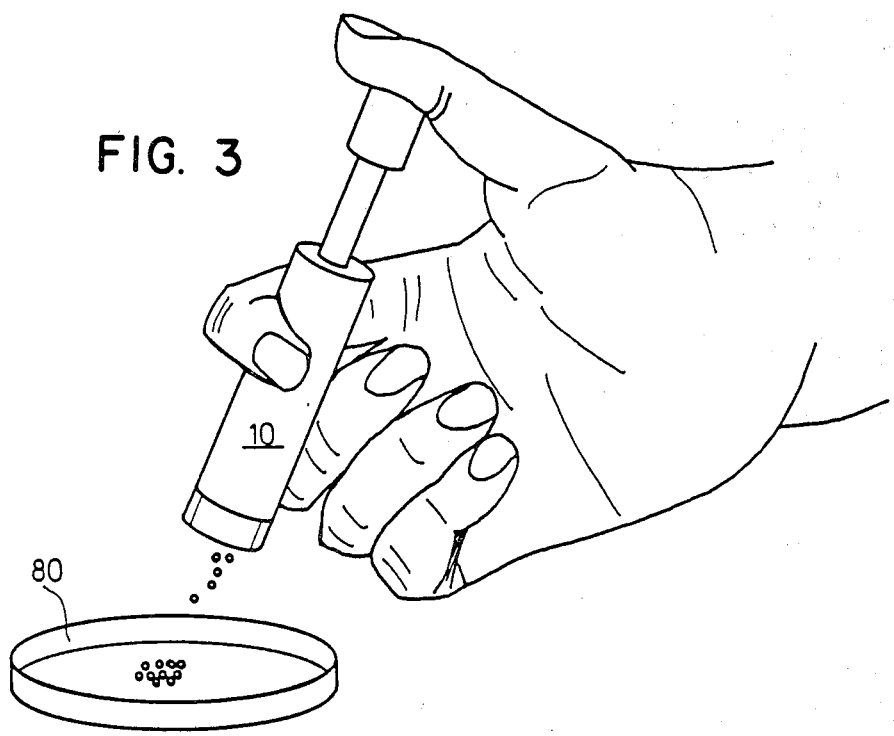
FIG. 3 is an illustration to explain the handling of the module.

This procedure is schematically illustrated in FIG. 3, in which 80 indicates a Petri dish containing an agar medium. Insofar as some of the absorbent 28 sticks together, it can, when it has been forced out of the cylindrical housing 12, easily be loosened with an appropriate instrument and thereby be finely measured and quickly distributed on to the Petri dish 80. This apparently simple improvement provides a considerable advance since, in the case of the identification of the micro-organisms causing a sepsis, it is important to be able to work quickly and in a sterile manner.

It will be understood that the specification and examples are illustrative but not limitative of the present invention and that other embodiments within the spirit and scope of the invention will suggest themselves to those skilled in the art.

What is claimed is:

1. In a device for use in the detection of at least one of bacteria, fungi, and viruses in blood, the device having a housing, particulate adsorbent capable of binding at least one of the bacteria, fungi, and viruses from blood flowing therethrough and suitable for subsequent use in at least one of bacteriological, virological, mycological, and electron-microscopic investigations in the housing, and means for connecting the housing into an extracorporeal blood circulation in such a way that the blood flows through the particulate adsorbant in the housing, the improvement comprising:
    a piston rod movably projecting through one side of the housing;
    piston means on the piston rod and in the housing for forcing at least part of the particulate adsorbent out of the housing; and
    a removable cover on another side of the housing such that, when the cover is removed and the piston rod moved into the housing, the piston means forces at least part of the particulate adsorbent out of the housing, whereby it is available for the investigations.

2. A device as in claim 1, wherein the piston means tapers toward the piston rod, and further comprising an O-ring so placed on the taper as to slip off irreversibly when the piston means is moved into the housing, whereby to indicate that the device has been used.

3. A device as in claim 1, wherein the piston rod has a pasage therethrough from outside to inside the housing at least before the piston rod is moved, the passage forming a part of the means for connecting the housing into the extracorporeal blood circulation.

4. A device as in claim 3, wherein the piston means tapers toward the piston rod, and further comprising an O-ring so placed on the taper as to slip off irreversibly when the piston means is moved into the housing, whereby to indicate that the device has been used.

5. A device as in claim 3, wherein the passage extends longitudinally throughout the piston rod.

6. A device as in claim 4, and further comprising three way valve means connected to the means for connecting the housing into the extracorporeal blood circulation for so connecting the housing, for switching the circulation to the housing to at least one of a flushing agent and nutrient broth, and for stopping circulation to the housing.

7. A device as in claim 5, wherein the piston means tapers toward the piston rod, and further comprising an O-ring so placed on the taper as to slip off irreversibly when the piston means is moved into the housing, whereby to indicate that the device has been used.

8. A device as in claim 4, wherein the passage terminates in the piston means, and wherein the piston means comprises a holding element permeable to the blood circulated into the passage and impermeable to the particulate adsorbent.

9. A device as in claim 8, wherein the holding element comprises a filter.

10. A device as in claim 8, and further comprising three way valve means connected to the means for connecting the housing into the extracoporeal blood circulation for so connecting the housing, for switching the circulation to the housing to at least one of a flushing agent and nutrient broth, and for stopping circuation to the housing.

11. A device as in claim 3, and further comprising three way valve means connected to the means for connecting the housing into the extracorporeal blood circulation for so connecting the housing, for switching the circulation to the housing to at least one of a flushing agent and nutrient broth, and for stopping circulation to the housing.

12. A device as in claim 3, wherein the passage terminates in the piston means, and wherein the piston means comprises a holding element permeable to the blood circulated into the passage and impermeable to the particulate adsorbent.

13. A device as in claim 12, wherein the piston means tapers toward the piston rod, and further comprising an O-ring so placed on the taper as to slip off irreversibly when the piston means is moved into the housing, whereby to indicate that the device has been used.

14. A device as in claim 12, wherein the holding element comprises a filter.

15. A device as in claim 12, and further comprising three way valve means connected to the means for connecting the housing into the extracorporeal blood circulation for so connecting the housing, for switching the circulation to the housing to at least one of a flushing agent and nutrient broth, and for stopping circulation to the housing.

16. A device as in claim 1, and further comprising three way valve means connected to the means for connecting the housing into the extracorporeal blood circulation for so connecting the housing, for switching the circulation to the housing to at least one of a flushing agent and nutrient broth, and for stopping circulation to the housing.

* * * * *

UNITED STATES PATENT AND TRADEMARK OFFICE
CERTIFICATE OF CORRECTION

PATENT NO. : 4,553,553
DATED : November 19, 1985
INVENTOR(S) : Ernst Homann et al.

It is certified that error appears in the above-identified patent and that said Letters Patent is hereby corrected as shown below:

Col. 1, line 53, delete "then removed,".

Col. 1, line 59, "corner" should be -- cover --.

Col. 3, line 14, "absorbent" should be -- adsorbent --.

Col. 4, line 25, "absorbent" should be -- adsorbent --.

Col. 5, line 24, "absorbent" should be -- adsorbent --.

Col. 6, Claim 6, line 1, "4" should be -- 5 --.

Signed and Sealed this

Twenty-fifth Day of March 1986

[SEAL]

Attest:

DONALD J. QUIGG

Attesting Officer     Commissioner of Patents and Trademarks